United States Patent [19]

Hopkins et al.

[11] 4,055,581
[45] Oct. 25, 1977

[54] HEAT AND LIGHT STABILIZERS FOR HALOGEN CONTAINING POLYMERIC RESINS

[75] Inventors: George C. Hopkins, Clarence, N.Y.; D. Bruce Merrifield, Houston, Tex.

[73] Assignee: Hooker Chemicals & Plastics Corporation, Niagara Falls, N.Y.

[21] Appl. No.: 631,967

[22] Filed: Nov. 14, 1975

Related U.S. Application Data

[63] Continuation-in-part of Ser. No. 430,115, Jan. 2, 1974, Pat. No. 3,933,740.

[51] Int. Cl.$^2$ ............................................. C07F 3/06
[52] U.S. Cl. ................................. 260/429.9; 260/537 R; 260/537 N; 560/130; 560/190
[58] Field of Search ............ 260/429.9, 537 R, 537 N, 260/479 S, 485 R, 485 J

[56] References Cited

U.S. PATENT DOCUMENTS

| | | |
|---|---|---|
| 2,378,629 | 6/1945 | Hanford ............................ 260/78.5 |
| 2,741,597 | 4/1956 | Oosterhout et al ............... 260/537 X |
| 2,811,551 | 10/1957 | Coffman et al. ................. 260/537 X |
| 3,068,195 | 12/1962 | Anderson et al. ............ 260/429.7 X |
| 3,136,748 | 6/1964 | Miller et al. ................. 260/485 R X |
| 3,231,587 | 1/1966 | Rense .............................. 260/537 X |
| 3,234,131 | 2/1966 | Morway ......................... 260/537 X |
| 3,271,310 | 9/1966 | Le Suer ....................... 260/429.9 X |
| 3,485,858 | 12/1969 | Gee et al. ........................ 260/429.9 |
| 3,542,778 | 11/1970 | Dillard et al. ............... 260/485 R X |
| 3,560,507 | 2/1971 | Wakeman et al. ............... 260/537 X |
| 3,629,205 | 12/1971 | Stamm ................................. 260/79.5 |
| 3,651,107 | 3/1972 | Stanback et al. ................ 260/429.7 |
| 3,933,740 | 1/1976 | Hopkins et al. ................ 260/45.75 |

FOREIGN PATENT DOCUMENTS 2,169,832   9/1973   France.

OTHER PUBLICATIONS

Encyclopedia of Polymer Science and Technology, vol. 12, pp. 741–742 (1970).
Modern Plastics Encyclopedia, Mar. (1969) vol. 41, No. 7, pp. 166 & 168.
Flett et al., Maleic Anhydride Derivatives, John Wiley & Sons, pp. 6–7 (1952).
Lenz, Organic Chemistry of Synthetic High Polymers, Interscience Publ., pp. 597–598 (1967).
Billmeyer, Textbook of Polymer Science, Wiley Interscience, 2nd Ed. p. 313 (1971).

*Primary Examiner*—Helen M. S. Sneed
*Attorney, Agent, or Firm*—P. F. Casella; J. F. Mudd; D. A. Stein

[57] ABSTRACT

A polymeric composition containing more than 5% halogen can be improved in heat and light stability by the incorporation therein of small amounts of a novel stabilizer which is the metallic salt of the reaction product of an alpha-olefin with maleic anhydride.

The stabilizers of the invention can be used either alone or in combination with conventional stabilizers for halogen containing polymeric materials.

9 Claims, No Drawings

HEAT AND LIGHT STABILIZERS FOR HALOGEN CONTAINING POLYMERIC RESINS

CROSS-REFERENCE TO RELATED APPLICATION

This application is a continuation-in-part of copending U.S. application Ser. No. 430,115 filed Jan. 2, 1974 now U.S. Pat. No. 3,933,740, issued Jan. 20, 1976.

BACKGROUND OF THE INVENTION

The present invention relates to stabilization of halogen containing polymers containing more than 5 weight percent halogen so as to provide improved heat and light stability therefor. Although not limited thereto, the present invention will be particularly described with respect to the stabilization of vinyl or similar polymers derived from vinyl chloride, vinyl acetate, vinyl chlroide acetate, vinylidene chloride, chlorostyrene or chlorobutadiene. The present invention is also applicable to resins which are post-halogenated or which are copolymerized with chlorinated or halogenated unsaturated hydrocarbons or their compounds, such as chlorinated polyethylene or its homologs and polymers, or chlorinated butadiene or styrene and their homologs and polymers.

It is known that chlorine containing resins such as polyvinyl chloride in which more than 5 weight percent chlorine is contained in the resin tend to be unstable toward the action of heat and light. Decomposition of the resin takes place unless temperatures used during formation and fabrication are kept below the temperature at which color formation begins. Currently available metallic stabilizer systems generally suffer from one or more of the following disadvantages: They are toxic (tin, barium and cadmium containing compositions). Upon utilization of certain stabilizers poor clarity of the polyvinyl chloride results (calcium and zinc containing salts). Some stabilizers are characterized by high cost (tin, barium, cadmium and calcium containing compositions). With many stabilizers currently commercially available, relatively low levels of stability are obtained by their use and even where large amounts are incorporated into the polyvinyl chloride, the efficiency of such stabilizers leaves much to be desired.

It is well known that calcium and zinc carboxylic acid salts function as stabilizers for polyvinyl chloride. Dihydrocarbyltin aliphatic-substituted succinates are discloses in U.S. Pat. No. 3,068,195 as useful to provide vinyl halide compositions which show improved resistance to light and heat.

The discoloration of polyvinyl chloride is thought to be due to liberation of hydrogen chloride which catalyzes further decomposition of the resin. The addition of basic compounds to neutralize the hydrogen chloride to form inert compounds should theoretically retard such discoloration and darkening. It has been found that many basic compounds are unsatisfactory and other similar compounds do not give the desired results as indicated by substantial darkening of the resin upon exposure to heat.

For example, lead, cadmium, manganese and calcium salts of high molecular weight, fatty acids, such as oleic, lauric, and palmitic; lead and cadmium salts of lower molecular weight fatty acids, such as the acetates; organic and inorganic bases, such as hydroxyl-amine and hexamethylene tetramine; alcoholates of alkali earth metals, such as calcium 2-ethyl hexylate; and calcium and cadmium salts of hexoic acids, when both an alkyl group or an ethyl group and a phenyl group ar directly attached to the alpha carbon atom, such as calcium phenylethylhexoate, cadmium pehnylethylhexoate and lead phenylethylhexoate, will permit substantial yellowing or darkening. The same is also true of cadmium salts of hexoic acid where an ethyl group only is attached to the alpha carbon atom. In general lead and cadmium salts are unsatisfactory and the same is true of alkali metal salts. Calcium, strontium and barium salts of straight chain unbranched acids or where the branched acid has a phenyl or aryl group attached directly to the alpha carbon atoms are also not entirely satisfactory.

The same difficulty has also been experienced with organo tin oxides or hydroxides; tetra-ethyl or tetra-butyl tin compounds; tetra-phenyl or propyl tri-phenyl lead and tin compounds; and dibutyl, tributyl and diphenyl tin acetates; oleates, laurates or stearates. Although these materials are useful in stabilizing halogen-containing vinyl resins, nevertheless incorporation of these materials does not prevent development of yellow color and eventual darkening or blackening of the resins, and furthermore use of these materials frequently results in development of a haze in heat pressed sheets.

With an adequate stabilizer incorporated into the polyvinyl chloride, an increased processing temperature can be utilized making possible high speed fabrication, including injection molding, extrusion, and blow molding of rigid polyvinyl chloride. The degradation noted upon exposure of polyvinyl chloride to elevated processing temperatures appears to result from a thermaloxidative dechydochlorination. Stabilizers have been incorporated into the polymer in order to retard or delay the initiation of propagation of the dehydrochlorination as well as to scavenge or react with the evolved hydrogen chloride. As indicated above, the stabilizers commonly used in the past have not been entirely satisfactory, and therefore it is the objective of the present invention to provide a process for the stabilization of compositions of polyvinyl halide having improved heat and light stability.

It is known to react an alpha-olefin with maleic anhydride to obtain an alkyl succinic anhydride. Such compounds, while having such varying uses as curing agents for epoxy resins, rust inhibitors, de-emulsifying agents, fungicides, plasticizers and surfactants, etc., have not been suggested for use either alone or further reacted as described herein as stabilizers for halogen containing resinous materials to reduce the tendency of these resins to discolor upon exposure to heat and light.

SUMMARY OF THE INVENTION

The invention comprises a halogenated polymeric resin having improved heat and light stability obtained by the incorporation therein of a stabilizer comprising the salt of multivalent or mixed metal salts of the reaction product or mixed reaction products of an alpha-olefin having preferably about 10 to about 20 carbon atoms and maleic anhydride or mono-substituted maleic anhydride, said reaction products being monomeric or polymeric of the formulas:

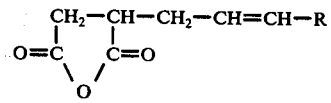

-continued

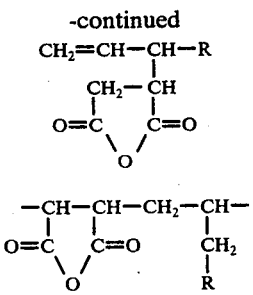

or mixtures thereof and wherein R is a hydrogen, aryl, alkyl, aralkyl, or alkylaryl radical or substituted derivative thereof which can be halogen substituted having 1 to 17 carbon atoms.

The invention is also directed to a process for stabilizing a halogen-containing polymeric resin and to new compositions of matter consisting of the stabilizer compositions.

DETAILED DESCRIPTION OF THE INVENTION AND OF THE PREFERRED EMBODIMENTS

A surprising discovery of the present invention is that a halogen-containing polymeric resin, such as polyvinyl chloride, can be stabilized by about 0.1% to about 10%, preferably about 0.5% to about 5% based upon said polymeric resin of the metal salts of the invention. It had been known to stabilize polyvinyl chloride resins against the action of heat and light by the use of metallic salts of monocarboxylic and dicarboxylic acids. These being monomeric compounds generally, it is surprising that the polymeric compounds of the invention function more effectively than the monomeric metallic salts of mono- and dicarboxylic acid previously used as stabilizers for polyvinyl cloride. It is also surprising that the allylic groups do not detract from the effectiveness of the stabilizer. Usually allylic groups set off free radical reactions that can degrade PVC. It appears that the allylic function, combined with the metal salts actually enhances stabilization in the stabilizers of the instant invention.

The stabilizers of the invention are prepared by converting the reaction product of an alpha-olefin with maleic anhydride or a mono-substituted maleic anhydride to the metal salts by hydrolysis or alcoholysis, followed by reaction with a base, as illustrated by the following typical series of reactions wherein the starting material is the monomeric substituted succinic anhydride resulting from the condensation of octadecene-1 and maleic anhydride:

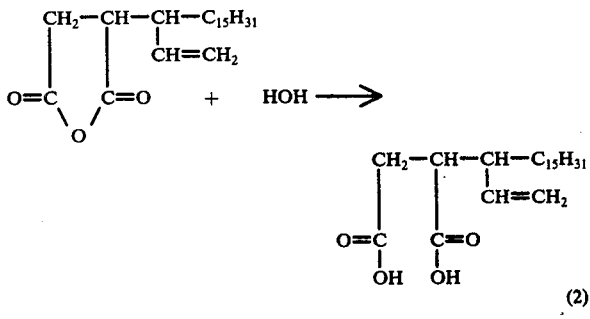

(1)

(2)

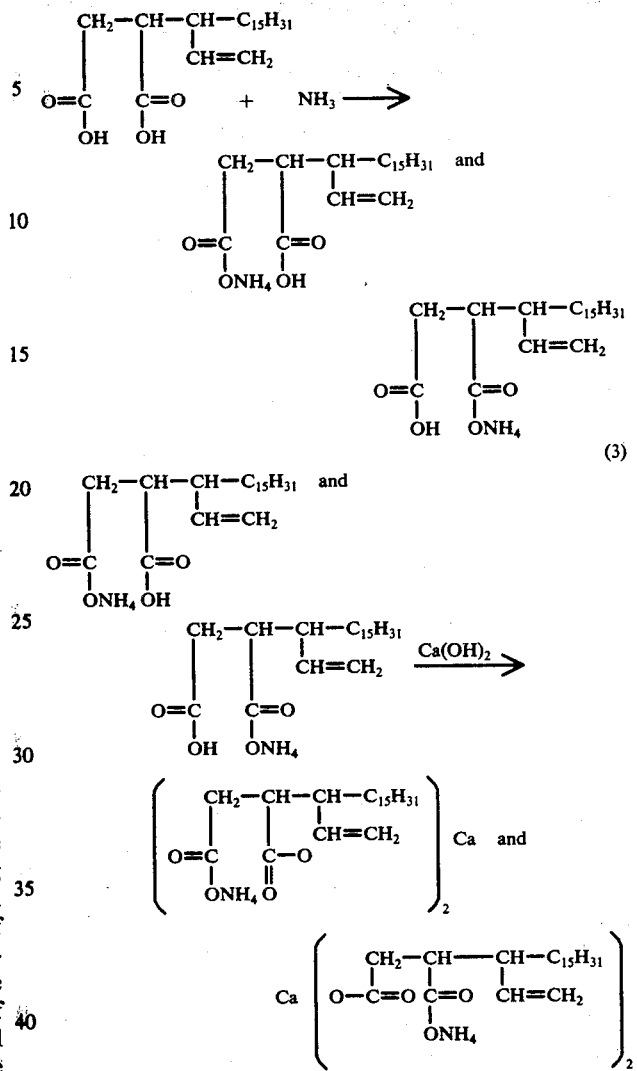

Since the polycarboxylic anhydride and its corresponding free carboxylic acid are unsymmetrically substituted in the hydrocarbon backbone, salt formation at the carboxylic acid groups with different salt forming positive ions, i.e., in this case, calcium and ammonium ions will provide calcium-ammonium salt products which can be represented as positional isomers as shown in the right hand side of equation (3) above. Analogous mixed salt products are obtained when the above monomeric substituted succinic anhydride reactant is replaced by a polymeric substituted succinic anhydride. e.g., the anhydride of the formula:

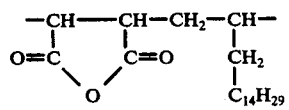

Salts useful in the practice of the invention can be obtained by reaction of the hydroxide of multivalent metals selected from the group consisting of calcium, zinc, cadmium, barium, and tin, with reaction products of an alphaolefin with maelic anhydride or mono-substituted derivative thereof.

The reaction product of an alpha-olefin with maleic anhydride or monosubstituted maleic anhydride is a known composition which can be prepared by the addition of one mole of of an olefin to one mole of maleic anhydride or substituted maleic anhydride. While an equimolar ratio of reactants is theoretically required, in order to maintain an effective addition reaction a molar excess of olefin is applied up to about 20 moles of olefin per mole of maleic anhydride. The reaction can be carried out by heating said reactants at a temperature above 160° C to about 300° C, preferably at a temperature of about 185° C to about 225° C over a period of time that can vary from about 0.1 to about 48 hours, preferably from about 2 to about 8 hours. Any suitable pressure, preferably pressures sufficient to maintain the reactants in the liquid phase can be employed up to about 1,000 pounds per square inch gauge, preferably from about 10 to about 500 pounds per square inch gauge.

Any olefin having from about three to about 60 carbon atoms can be employed in the reaction with the maleic anhydride, although alpha-olefins having from about six to about 30 carbon atoms, preferably from about ten to about 20 carbon atoms can be employed. Examples of such olefins are propylene, butene-1, pentene-1, hexene-1, heptene-1, octene-1, nonene-1, decene-1, undecene-1, dodecene-1, tridecene-1, tetradecene-1, pentadecene-1, hexadecene-1, heptadecene-1, octadecene-1, nonadecene-1, eicosene-1, heneicosene-1, docosene-1, tricosene-1, tetracosene-1, pentacosene-1, hexacosene-1, heptacosene-1, octacosene-1, nonacosene-1, triacontene-1, hentriacontene-1, dotriacontene-1, tritriacontene-1, tetratriacontene-1, none-3, decene-4, 7-methyldecene-2, 7-mehtyldecene-1, 6,9-diethylundecene-1, 5,7-dimethyldodecene-1, 4,7,9-trimethyltridecene-1, 5-butyltetradecadiene-1,5, 8-phenylpentadecene-1, 7-cyclohexylhexadecene-1, 11(alpha-cumyl)heptadecene-1, 6-butyloctadecadiene-1,11, 5-(2-norbornyl)nonadecene-1, 6-ethyleiscosene-1, 8-t-butyltricosene-1, 7-phenyldocosene-1, 4-methyloctene-1, 4-methylpentadecene-1, 5-mehtylpentadecene-1, 8-methylpentadecene-1, 9-methylpentadecene-1, 10-phenyldecene-1, 10-cyclohexyldecene-1, 10-cyclooctyldecene-1, 4,5,6,7-tetramethylcotene-1, 4,6,7-trimethyldecene-1, 4,6,7-trimethyldodecent-1, 9-chlorononene-1, 5-methoxydecene-1, 7,11-diphenylundecene-1, 11-dodecenal-1, 8-ketotridecene-1, decene-2, 14-cyanopentadecene-1, 10-undecenoic acid, 15-n-hexadecenoic acid, isooctyl 16-m-heptadecanoxadodecene-1, 4,7-dimethyltridec-1-ene-9,11,12-tetracarboxylic dianhydride, 4-butyltetradecadiene-1,5, 8-(p-chloromercuriphenyl)pentadecene-1, 7-(4-nitrocyclohexyl)hexadecene-1, 11-(alpha-cumyl)heptadecene-1, 6-(paraisopropylphenyl)decene-1, 5-(2-norbornyl)nonadecene-1, 6-butyloctadedaciene-1, 11, 8-tertiarybutyl-12-(2,4-dichloromethyl-tetradecene-1, 7-phenyl-10(2-[6,6-dibromo-3-oxabicyclo(3.1.0-)hexyl])docosene-1, 4-methyloctene-1, 4-methylpentadecatetrane-1,4,7,12, diethyl-14-pentadecenyl-succinate, 8-diazomethyl pentadecene-1, 9-carboxymethyl pentadecene-1, 10-(2,3-diiophenyl)decene-1, 10-(2,4-cyclohexadienyl)decene-1, 10-cyclopentyldecadiene-1,10,4,7-diketo-10-cyclooctyldecene-1, 4,5,6,7-tetrachloromethyloctene-1, 4,6,7-trinitromethyldecene-1, 4,6,7-triphenoxymethyl dodecene-1, tricontene-1, hexacontene-1, etc. The maleic anhydride used can be maleic anhydride itself or a monosubstituted maleic anhydride, such as citraconic anhydride, ethylmaleic anhydride, ethylmaleic anhydride, methoxymaleic anhydride, etc.

The reaction product at the end of the reaction period can be treated in any suitable manner such as by distillation to recover the individual components therefrom, or the crude mixture can be utilized in forming the metallic salt stabilizer of the invention. Thus, the reaction product can be distilled at a temperture of about 50° to about 250° C. and a pressure of about $10^{-4}$ to about 15 pounds per square inch gauge to recover separately therefrom unreacted olefin, unreacted maleic anhydride, if present; and the desired alkenyl succinic anhydride.

The anions of the polymeric salts of the invention can range in size from dimers or trimers of the substituted succinate monomeric anion to a molecular weight of about 1,000,000 or more.

The metallic salt of the alkenyl succinic anhydride can be obtained by hydrolysis or alcoholysis, followed by reaction with a base to obtain metal salts of the invention, essentially comprised of monomeric and polymeric salts, the general formulas of the monomeric salts being illustrated in the left hand column below with the general formulas of the recurring units of the polymeric salts being illustrated in right hand column below:

Monomeric Salts

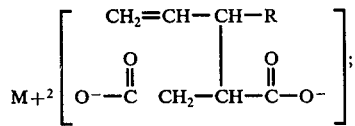

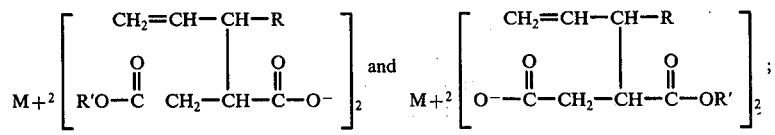

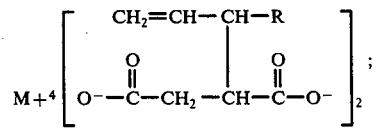

-continued

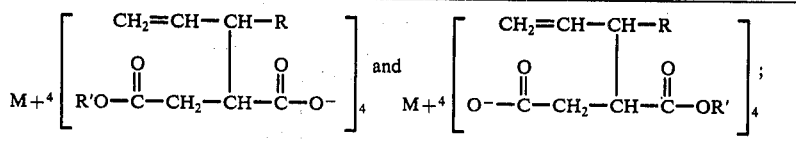

and

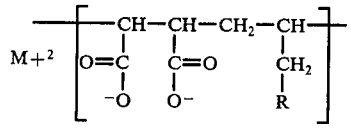

Polymeric Salts

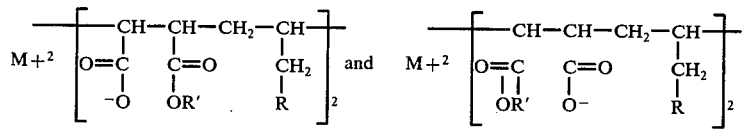

and

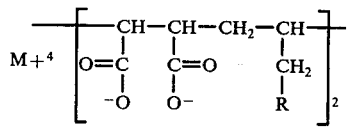

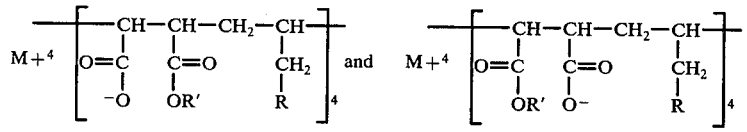

and

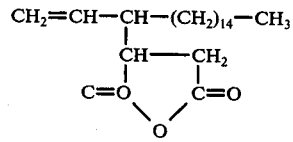

In the above general formulas, M and R are as defined above and R' is selected from the group consisting of monovalent cations, hydrogen, alkyl, aralkyl, aryl and alkaryl having 1 to 17 carbon atoms, or substituted derivatives thereof which can be halogen substituted derivatives having 1 to 17 carbon atoms. By monovalent cation is meant a univalent ion of an alkali metal, i.e., a metal of Group IA of the Periodic Table, such as potassium, sodium, rubidium and the like, or ammonium ion or lower alkylammonium ion, i.e., ammonium ion with one, two, three or four straight or branched chain aliphatic hydrocarbon groups exemplified by methylammonium, dimethyl ammonium, tetramethyl ammonium, tetra-sec butyl ammonium, tri-n-hexyl ammonium, dimethyl, di-ethyl ammonium, isopropyl ammonium, tetra n-amyl ammonium, tri-n-propyl ammonium and tetra-ethyl ammonium. By varying the substituents represented by R and R' with M representing a multivalent metal as previously defined, it is possible to prepare stabilizer systems having a wide variety of properties so as to provide improved compatibility in polyvinyl chloride compounds, and to provide stabilizer properties in combination with plasticizer action or even to provide compounds which can function as lubricants for the polyvinyl chloride. the metal salt derivatives of the alkenyl succinic anhydride are relatively inexpensive in comparison to commercial stabilizer compositions since the main raw materials (alpha-olefins and maleic anhydride) are both inexpensive compounds. Compositions of the invention can be used in combination with chelating agents for their known effects.

The utility and advantages of the stabilizers of the invention as well as of the resin compositions stabilized therewith will furher become apparent from the following examples which are included to illustrate the practice of the invention but not to limit the invention.

In these examples, as well as throughout the specification and claims, all parts and percentages are by weight, all pressures are gauge pressures, and all temperatures are in degrees centigrade unless otherwise specified.

EXAMPLE 1

An adduct of maleic anhydride and octadecene-1 is prepared by first charging an autoclave with 303 grams (1.20 mols) of octadecene-1 and 117.6 grams (1.20 mols) of maleic anhydride. The autoclave is then sealed and the air evacuated and then the autoclave is purged with nitrogen several times prior to heating under vacuum to 250° C for 12 hours while stirring. Approximately 120 pounds per square inch pressure, gauge, develops. The autoclave is then cooled to room temperature and the contents are distilled in vacuum to give 235 grams (56% yield) of a waxy, white solid having a melting point of 63° to 66° C, which is identified by infrared, nuclear magnetic resonance and molecular weight analysis as having a structure consisting of the following:

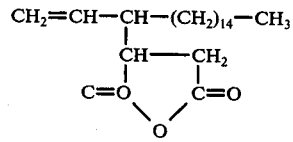

EXAMPLE 2

The calcium salt of the alkenyl succinic anhydride prepared in Example 1 is formed by slurrying in hot water for approximately 4 hours calcium hydroxide, 0.148 grams (2.00 × 10⁻³ mole) and 0.701 grams (2.00 × 10⁻³ mole) of the alkenyl succinic anhydride of Example 1. The product is separated by filtration to give and 87% yield of white solid having a melting point of greater than 270° C and having the following probable structure based upon infrared analysis.

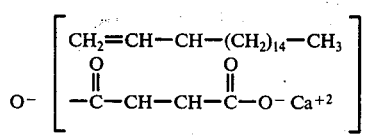

EXAMPLE 3

The zinc salt of the alkenyl succinic anhydride prepared in Example 1 is formed by essentially the same procedure as used to prepare the calcium salt except that calcium hydroxide is replaced by zinc carbonate, which is used in the same molar amount, namely, an equimolar amount based upon the alkenyl succinic anhydride. An 80% yield of a white zinc salt is obtained having the following probable structure based upon infrared analysis:

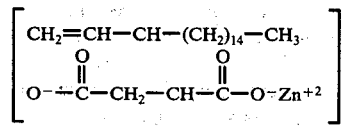

EXAMPLE 4

Polyvinyl chloride films are stabilized using the stabilizer compositions of the invention by combining a powdered polyvinyl chloride resin with varying amounts of stabilizer as indicated in Table 1 below. The powdered resin plus the stabilizer is made into a film by heating the composition at 200° C and 6,000 pounds per square inch, gauge, for 2 minutes. The preparation of such a film constitutes a quick and easy test for thermal stability since the color and general film condition can be recorded and compared with corresponding films having different compositions with respect to stabilizer content. Observation of color development in such heated and pressed films of polyvinyl chloride is a very sensitive method of screen testing for heat stability, as is well known. The results of the tests show, as indicated in Table 1 below, that the calcium salt of the alkenyl succinic anhydride when used in combination with polyvinyl chloride is superior to the use of an equal quantity of calcium stearate (a commercial stabilizer). The corresponding zinc salt can be used as a secondary stabilizer.

TABLE I
Heat Stabilization of Polyvinyl Chloride

| Stabilizer | Amount Used | (200° C/6000 psi/2 Mins.) Film Color and Clarity |
|---|---|---|
| No Stabilizer | — | Red Orange - clear |
| Example 2 | 3 PHR | Pale Yellow - cloudy |
| Example 3 | 0.10 ⎫ PHR | Slightly green - slightly cloudy |
| Example 2 | 2.75 ⎭ | Yellow -cloudy |
| Calcium stearate | 3 PHR | Pale Orange - very cloudy |

EXAMPLE 5

A mixed calcium-sodium salt of an alkenyl succinic acid is prepared by combining under agitation in hot water about 0.08 grams (2.0 × 10⁻³ mole) of sodium hydroxide and about 0.701 grams (2.00 × 10⁻³ mole) of the alkenyl succinic anhydride prepared in Example 1. After agitation of the resulting mass for about four hours, about 0.074 grams (1.0 × 10⁻³ mole) of calcium hydroxide is charged and the resultant slurry is agitated for an additional four hours. The resultant slurry is then filtered to collect an excellent yield of the solid product which can be represented as being essentially a mixture in about equal proportions of the isomeric salts of the formulas:

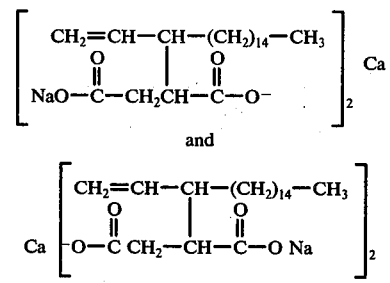

EXAMPLE 6

The procedure of Example 5 is repeated substantially as described except that an equivalent molar proportion of ammonia is employed as inorganic base in place of sodium hydroxide. The product obtained is a mixed calcium — ammonium salt of the alkenyl succinic acid which can be represented as being essentially a mixture in about equal proportions of the isomeric salts of the formulas:

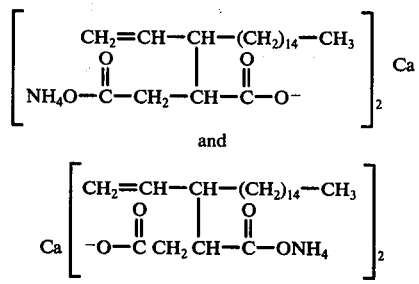

EXAMPLE 7

Test samples of vinyl chloride films are stabilized with the calcium-sodium salt products of Example 5 and the calcium-ammonium salt products of Example 6 following the procedure of Example 4. When tested for heat stability by the color development test described in Example 4, the present test samples exhibit low color development substantially similar to the results of the tests reported in the second, third and fourth lines of Table 1. The present results are hence indicative of the excellent heat stabilizing properties of the calcium containing salts of Examples 5 and 6.

While this invention has been described with reference to certain specific embodiments, it will be recognized by those skilled in the art that many variations are possible without departing from the scope and spirit of the invention.

What is claimed is:

1. As stabilizer for halogen-containing polymers, a metal salt selected from the group consisting of metal salts of the polymeric and monomeric reaction products of an alpha olefin and maleic anhydride, said polymeric metal salt having recurring units of the formula:

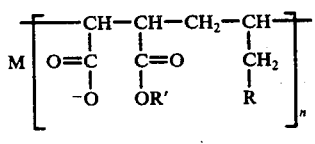  (A)

or

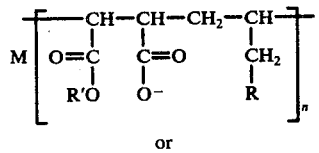  (B)

or

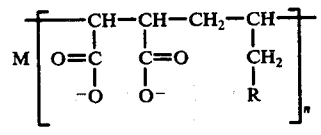  (C)

and said metal monomeric salt being represented by the formula:

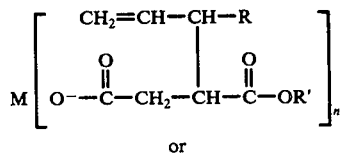  (D)

or (E)

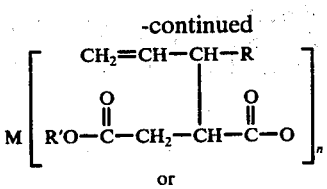

or

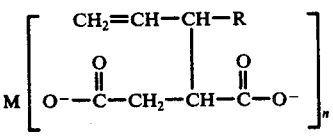  (F)

or mixtures thereof wherein M represents a di- or tetravalent metal selected from the group consisting of calcium, zinc, cadmium, barium and tin; n is 1 or 2 in formulas (C) and (F) and 2 or 4 in formulas (A), (B), (D), and (E); R is selected from the group consisting of hydrogen, aryl, alkyl, aralkyl, alkaryl and substituted derivatives thereof having 1 to 17 carbon atoms which can be halogenated, and R' is selected from the group consisting of alkali metal cations, ammonium cation, lower alkyl-substituted ammonium cations, hydrogen atom, aryl groups, alkyl groups, aralkyl groups, alkaryl groups and substituted derivatives of said groups having 1 to 17 carbon atoms which can be halogenated.

2. The composition of claim 1 wherein M is zinc.
3. The composition of claim 2 wherein R is n-$C_{14}H_{29}$.
4. The composition of claim 1 wherein M is calcium.
5. The composition of claim 4 wherein R is n-$C_{14}H_{29}$.
6. The composition of claim 5 wherein R' is ammonium.
7. The composition of claim 5 wherein R' is sodium.
8. The composition of claim 3 wherein the structure of the salt corresponds essentially to formula (F).
9. The composition of claim 5 wherein the structure of the salt corresponds essentially to formula (F).

* * * * *